US 11,406,348 B2

(12) United States Patent
Kjær Thing Riknagel et al.

(10) Patent No.: US 11,406,348 B2
(45) Date of Patent: *Aug. 9, 2022

(54) METHOD OF DETECTING DICROTIC NOTCH

(71) Applicant: VIEWCARE TECHNOLOGIES 1 APS, Søborg (DK)

(72) Inventors: Diana Kjær Thing Riknagel, Jedsted (DK); Johannes Jan Struijk, Terndrup (DK); Henrik Zimmermann, Aalborg (DE)

(73) Assignee: VIEWCARE TECHNOLOGIES 1 APS, Søborg (DK)

(*) Notice: Subject to any disclaimer, the term of this patent is extended or adjusted under 35 U.S.C. 154(b) by 363 days.

This patent is subject to a terminal disclaimer.

(21) Appl. No.: 16/803,900

(22) Filed: Feb. 27, 2020

(65) Prior Publication Data
US 2020/0253577 A1    Aug. 13, 2020

Related U.S. Application Data

(63) Continuation of application No. 15/518,117, filed as application No. PCT/EP2015/073996 on Oct. 16, 2015, now Pat. No. 10,575,814.

(30) Foreign Application Priority Data

Oct. 16, 2014   (SE) .................................. 1451240-4

(51) Int. Cl.
A61B 7/04        (2006.01)
A61B 5/00        (2006.01)
(Continued)

(52) U.S. Cl.
CPC ............ A61B 7/04 (2013.01); A61B 5/02007 (2013.01); A61B 5/02411 (2013.01);
(Continued)

(58) Field of Classification Search
CPC ... A61B 7/04; A61B 5/02007; A61B 5/02411; A61B 5/4362; A61B 5/6833;
(Continued)

(56) References Cited

U.S. PATENT DOCUMENTS 6,261,238 B1    7/2001  Gavriely
2002/0052553 A1  5/2002  Shalman et al.
(Continued)

FOREIGN PATENT DOCUMENTS

CN    1929777 A     3/2007
CN    103491868 B   5/2016
(Continued)

OTHER PUBLICATIONS

Antonelli, L., et al., "Dicrotic Notch Detection Using Wavelet Transform Analysis," Proceedings of the 16th Annual International Conference of the IEEE: Engineering in Medicine and Biology Society, Baltimore, Nov. 3-6, 1994, pp. 1216-1217.
(Continued)

Primary Examiner — Jonathan T Kuo
(74) Attorney, Agent, or Firm — Christensen O'Connor Johnson Kindness PLLC

(57) ABSTRACT

A method for assessment and/or monitoring a person's cardiovascular state comprises: using a sound and vibration transducer to acquire a vascular sound signal in order to detect a vascular sound from a cervical, thoracic, abdominal, pelvic, or lower limb region of the person; filtering the vascular sound signal to isolate the vascular sound, said filtering using a filter which attenuates frequencies below a lower cut-off frequency in a range of 100-300 Hz; and
(Continued)

analyzing the filtered sound signal in order to determine whether an indication of a dicrotic notch in the vascular sound exceeds a set threshold.

24 Claims, 3 Drawing Sheets

(51) Int. Cl.
| | | |
|---|---|---|
| *A61B 7/02* | (2006.01) | |
| *A61B 5/02* | (2006.01) | |
| *A61B 7/00* | (2006.01) | |
| *A61B 5/024* | (2006.01) | |

(52) U.S. Cl.
CPC .......... *A61B 5/4362* (2013.01); *A61B 5/6833* (2013.01); *A61B 5/725* (2013.01); *A61B 7/00* (2013.01); *A61B 7/026* (2013.01); *A61B 5/02* (2013.01); *A61B 5/4343* (2013.01); *A61B 5/6802* (2013.01)

(58) Field of Classification Search
CPC ........... A61B 5/725; A61B 7/00; A61B 7/026; A61B 5/02; A61B 5/4343; A61B 5/6802
See application file for complete search history.

(56) References Cited

U.S. PATENT DOCUMENTS

| | | |
|---|---|---|
| 2003/0004421 A1 | 1/2003 | Ting et al. |
| 2007/0260155 A1 | 11/2007 | Rapoport et al. |
| 2008/0183232 A1 | 7/2008 | Voss et al. |
| 2010/0228136 A1 | 9/2010 | Keel et al. |

FOREIGN PATENT DOCUMENTS

| | | |
|---|---|---|
| EP | J 968 681 A1 | 1/2000 |
| EP | 2 829 223 A1 | 1/2015 |
| WO | 2008/132751 A2 | 11/2008 |
| WO | 2013/079073 A1 | 6/2013 |

OTHER PUBLICATIONS

Faber, R., et al., "Analysis of Blood Pressure Waveform: A New Method for the Classification of Hypertensive Pregnancy Disorders," Journal of Human Hypertension 18(2): 135-137, Feb. 2004.
International Search Report and Written Opinion dated Jan. 19, 2016, issued in corresponding International Application No. PCT/EP2015/073996, filed Oct. 16, 2015, 13 pages.
Swedish Office Action dated May 22, 2015, issued in corresponding Application No. SE 1451240-4, filed Oct. 16, 2014, 7 pages.

METHOD OF DETECTING DICROTIC NOTCH

CROSS-REFERENCES TO RELATED APPLICATIONS

This application is a continuation of U.S. patent application Ser. No. 15/518,117, filed Apr. 10, 2017, which is the national stage of International Patent Application No. PCT/EP2015/073996, filed Oct. 16, 2015, both of which applications are expressly incorporated herein by reference in their entirety.

BACKGROUND

The present invention relates to a method and a device for assessing and monitoring cardiovascular health in humans. Cardiovascular impairments are the main cause of death in the western world. Cardiovascular problems are often related to or accompanied by stenosis in arteries, increase of arterial stiffness, hypertension, or other vascular changes, be it anatomical or physiological.

Assessment of the vascular system of humans has been subject of more than a century of research and development. Blood pressure measurements using the well-known sphygmomanometer, assessment using ultrasound (including Doppler), various ways of measurement of pressure waves, plethysmography and angiography have been used both clinically and in research.

However, there are one or more problems associated with all of the above known measurement methods. The known measurement methods may be expensive, such as ultrasound assessment and plethysmography, and/or invasive, such as angiography. Further, there may be a need to obtain more information than possible with the known measurement methods. For instance, the measurement methods may only obtain limited information on the vascular tree, such as when using a sphygmomanometer. Further, the known measurement methods may not give information about a part of the vascular system that actually matters.

It may often be important to obtain information about the central, abdominal or big arteries, such as aorta, carotid arteries, iliac arteries with branches, renal arteries, mesenteric arteries, and femoral arteries. Such information may provide an indication of a state of health/disease or may be used for assessment of medication induced changes to the vascular system. For instance, assessment or monitoring of the vascular system may be needed in relation to use of vasodilatory drugs, in assessing vascular disease, including coronary artery disease and diastolic dysfunction, in anesthesiology/intensive care for monitoring cardiac output, diabetes, kidney disease, rheumatoid arthritis, hypercholesterolemia, hyperlipidemia, or exercise monitoring.

The assessment and monitoring of the vascular system may present different problems depending on the particular use of the assessment and monitoring.

A specific area of interest is assessment and monitoring of cardiovascular changes in relation to pregnancies, births, and post-partum changes. There is a great interest in accomplishing early detection of any complications related to a pregnancy.

In particular, the vascularization of the uterus and the placenta of the pregnant woman may provide indications of the cardiovascular risk of the pregnant woman, and also whether the fetus is developing normally. It is possible to measure the blood flow of uterine and umbilical arteries of the pregnant woman using Doppler velocimetry. However, this requires the use of ultrasound scanning equipment, and the measurement needs to be performed by trained medical staff. Hence, the measurement of the blood flow may only be performed on occasion, requiring the pregnant woman to come to a clinic and involving medical staff for performing the measurement, and with the risk of undiscovered cardiovascular deterioration in the meantime.

Typically, monitoring of uterine and umbilical arterial blood flow is only started, when it is detected by other means that the fetus may not be developing normally or when the pregnant woman belongs to a high risk group. Monitoring may thus be used in cases such as: Intra Uterine Growth Restriction (IUGR), twin pregnancy, maternal hypertension, maternal pre-eclampsia, maternal diabetes, placental insufficiency leading to premature birth, miscarry or stillbirth, and women pregnant after In Vitro Fertilization (IVF).

When diagnosed as having a fetus not developing normally or belonging to a high risk group, the pregnant woman may become anxious and worry about the state of the fetus. The woman may therefore frequently ask for examinations to check the state of the fetus, whereby hospital resources are demanded each time an examination is made. Further, the nervous tension felt by the pregnant woman may also act to aggravate the condition, for instance when the pregnant woman suffers from pre-eclampsia or hypertensive disorder. Therefore, any method for allowing the pregnant woman to make an examination at home would be beneficial both in terms of medical resources required and in providing a possibility for the pregnant woman to check the condition of the fetus whenever worries arise.

Also, the sensitivity of uterine artery Doppler velocimetry using ultrasound increases proportionally with early onset of the clinical manifestations of IUGR and pre-eclampsia and with their severity, but the Doppler velocimetry has a low specificity which may lead to expected iatrogenic premature births and unnecessary interventions in the pregnancy contributing to maternal and neonatal morbidity and mortality.

Preeclampsia is one of the leading causes of pregnancy related maternal morbidity and mortality. In addition to the immediate risk, women who recover from preeclampsia are more likely to experience life-threatening cardiovascular disease later in life. The cardiovascular risk in preeclampsia is associated with increased central arterial stiffness and measures of arterial function as pulse wave analysis or pulse wave velocity (as increased carotid or femoral pulse wave velocity) is useful for clinical assessments.

As is evident from the above, it would be desirable to provide an improved method for continuously assessing the cardiovascular status of the pregnant woman and the development of a fetus. In particular, it would be desirable to provide a method that does not require medical staff to perform measurements and which may be performed by the pregnant woman in her home.

WO 2013/079073 discloses a system for monitoring a fetus in a pregnant woman. The system comprises a portable unit that can be worn by the pregnant woman so as to allow monitoring during daily life. The portable unit has a sound sensor to be positioned on the skin of the abdominal area of the pregnant woman so as to detect a vascular sound from the umbilical arteries of the fetus or from the uterine arteries of the pregnant woman. The sound sensor is functionally connected to a processing unit which executes a processing algorithm on the captured vascular sound and extracts a signal parameter accordingly.

The system allows a measurement of vascular sound to be made by means of a sound sensor that may be worn by the pregnant woman during daily life. Hence, the system may reduce the need for the pregnant woman to be examined at a medical clinic and may also reduce anxiety of the pregnant woman as the state of the fetus may be continuously monitored.

Although the technology disclosed in WO 2013/079073 may enable monitoring of a pregnant woman in her home, there is still room for improvement in the analysis of the vascular sound in order to determine a condition of the fetus.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

It is an object of the invention to provide an improved method for assessing and/or monitoring of cardiovascular health in humans. It is a further object of the invention to enable use of an improved analysis for detection of a vascular condition and to enable continuous monitoring of the condition.

These and other objects of the invention are at least partly met by the invention as defined in the independent claims. Preferred embodiments are set out in the dependent claims.

According to a first aspect of the invention, there is provided a method for assessment and/or monitoring of a person's cardiovascular state, the method comprising: using a sound and vibration transducer to acquire a vascular sound signal in order to detect a vascular sound from a cervical, thoracic, abdominal, pelvic or lower limb region of the person; filtering the vascular sound signal to isolate the vascular sound, said filtering using a filter which attenuates frequencies below a lower cut-off frequency in a range of 100-300 Hz; and analyzing the filtered sound signal in order to determine whether an indication of a dicrotic notch in the vascular sound exceeds a set threshold.

According to a second aspect of the invention, there is provided a device for assessment and/or monitoring of a person's cardiovascular state, the device comprising: a sound and vibration transducer, which is arranged to be positioned in relation to a cervical, thoracic, abdominal, pelvic, or lower limb region of the person so as to acquire a vascular sound signal in order to detect a vascular sound from the region of the person; and a processing unit, which is arranged to receive the vascular sound signal from the sound and vibration transducer and which is further configured to process the vascular sound signal by: filtering the vascular sound signal to isolate the vascular sound, said filtering using a filter which attenuates frequencies below a lower cut-off frequency in a range of 100-300 Hz; and analyzing the filtered sound signal in order to determine whether an indication of a dicrotic notch in the vascular sound exceeds a set threshold.

According to the invention, there is provided a method and device for acquiring vascular sounds originating from blood flow through arteries of a person. The vascular sounds may be obtained by means of a passive device that detects the sounds of blood flow and there is therefore no necessity to provide a signal into the person's body so as to detect a response to the signal. Further, there is no need for a clinician or other medically trained personnel to perform or trigger the acquiring of vascular sounds. Hence, the invention facilitates for continuous acquiring of vascular sounds such that it may provide continuous assessment or monitoring of the cardiovascular health of a person. The person may even wear or carry the device during daily life so that assessment or monitoring of the cardiovascular health may be provided at all times and an alert may be created when attention is needed to the condition of the person.

Although the invention may be especially suited for use in continuous monitoring of the cardiovascular health of a person, the invention may also be used in assessing the cardiovascular health of a person at a specific point of time, such as in an examination by a caregiver or during a surgery or other medical procedure.

According to the invention, a filter is used for attenuating frequencies below a lower cut-off frequency in a range of 100-300 Hz. This implies that sounds originating from a beating heart may be suppressed and that the filtered sound signal may relate to blood flow through arteries of the person. Hence, vascular sound signals may be acquired from a specific region of a person by means of placing a sound and vibration transducer in the specific region. Then, the acquired sound signals may relate to the blood flow in the specific region allowing analysis of the condition of the specific region.

According to the invention, a vascular sound signal is obtained, which is different from signals obtained by traditional, active methods wherein a signal is actively emitted into the person, such as in ultrasound examinations. Hence, analysis made on signals obtained through such traditional, active methods may not be directly transferred to the passive acquiring of vascular sound according to the invention.

The filtered vascular sound signal may comprise characteristics relating to a dicrotic notch. The dicrotic notch relates to a dip in aortic pressure that occurs in cardiac cycle after contraction of the ventricles and coincides with closure of the aortic valve, which prevents blood from flowing back into the ventricles. Blood vessels have elastic walls, which implies that blood flow distal to the aorta will be leveled out and be fairly constant. However, for people having relatively inelastic walls, the blood flow will not be leveled out as quickly distal to the aorta and the pulsatile characteristic of blood flow will be evident in distalarteries.

It is an insight of the invention that the filtered sound signal may be analyzed in order to determine characteristics of the dicrotic notch. Further, an indication of the dicrotic notch exceeding a set threshold may be related to a physical condition of the person, such as hypertension.

In the context of this application, vascular sound should be construed as any signal caused by blood flow through a blood vessel. Such signal will propagate through tissue of the person such that it may be detected by a sensor being positioned in relation to a region of interest of the person. The signal may be detected by means of a microphone arranged in close relationship to the person's skin, the microphone being able to convert air pressure variations to an electrical signal. However, the sound and vibration transducer may be arranged in a number of different manners for detecting the signal as air pressure variations or as vibrations on the skin surface. For instance, the sound and vibration transducer may be implemented as a microphone and air coupler, wherein the vibration on the surface of the skin is translated to a small air pressure inside the air coupler and the air pressure is recorded by the microphone. Alternatively, the sound and vibration transducer may be implemented as an accelerometer or a piezoelectric sensor attached to the surface of the skin.

According to a third aspect of the invention, there is provided a method for assessment and/or monitoring of a pregnant woman and/or a fetus in a pregnant woman, the method comprising: using a sound and vibration transducer to acquire a vascular sound signal in order to detect a vascular sound from an abdominal or pelvic region of the pregnant woman; filtering the vascular sound signal to isolate the vascular sound, said filtering using a filter which attenuates frequencies below a lower cut-off frequency in a range of 100-300 Hz; and analyzing the filtered sound signal in order to determine whether an indication of a dicrotic notch in the vascular sound exceeds a set threshold.

According to a fourth aspect of the invention, there is provided a device for assessment and/or monitoring of a pregnant woman and/or a fetus in a pregnant woman, the device comprising: a sound and vibration transducer, which is arranged to be positioned in relation to an abdominal or pelvic region of the pregnant woman so as to acquire a vascular sound signal in order to detect a vascular sound from the abdominal or pelvic region of the pregnant woman; and a processing unit, which is arranged to receive the vascular sound signal from the sound and vibration transducer and which is further configured to process the vascular sound signal by: filtering the vascular sound signal to isolate the vascular sound, said filtering using a filter which attenuates frequencies below a lower cut-off frequency in a range of 100-300 Hz; and analyzing the filtered sound signal in order to determine whether an indication of a dicrotic notch in the vascular sound exceeds a set threshold.

It is an object of the third and fourth aspect of the invention to provide an improved analysis of captured vascular sound and relating the vascular sound to a condition of a fetus or a pregnant woman.

The third and fourth aspect of the invention relates to a particular application, wherein vascular sound signals are acquired for analysis in relation to a pregnancy.

According to these aspects of the invention, there is provided a method and a device for monitoring a pregnant woman or a fetus in a pregnant woman using passive technology. There is no need of providing a signal or any kind of stimulation into the pregnant woman's body in order to listen to a response to the signal or stimulation, which is e.g. done in an ultrasound examination. Rather, sounds that are normally occurring in the pregnant woman are acquired and analyzed. This implies that there may be no need for an operator handling the equipment for performing the analysis and, in fact, the analysis may be performed continuously by the pregnant woman wearing a sound and vibration transducer during daily life.

The invention makes use of vascular sounds that stem from the blood supplying the fetus in the pregnant woman. It might not be possible to derive from exactly what artery the vascular sounds that are acquired originate. However, it may be assumed that the vascular sounds originate from a main artery in the abdominal or pelvic region of the pregnant woman, such as a uterine artery, an umbilical artery or an iliac artery. Regardless, according to the invention, it is possible to acquire vascular sound that may be analyzed by means of a sound and vibration transducer, which may be positioned in relation to the abdominal or pelvic region of the pregnant woman.

It is further an insight of the invention that the filtered vascular sound signal may be analyzed in order to relate an indication of a dicrotic notch in the vascular sound exceeding a set threshold to a condition of a fetus or a pregnant woman. For instance, in pregnant women, the blood flow increases to vascularize the uterus and placenta to satisfy the metabolic demands of the fetus and to meet the requirements of gas-exchanging to the fetal vascular system. The uterine arteries will go through structural enlargement during pregnancy, so that from gestational week 24, the uterine arteries should be adapted to the increased blood flow. If the structural enlargement of the uterine arteries does not occur (or only partly occurs), the increased total blood volume is forced through the arteries by increased velocity and an indication of the dicrotic notch may persist from early pregnancy. The dicrotic notch may also occur when other pathology or external induced changes occur, such as endocrine changes, hypertension, diabetes, heavy smoking, etc. Therefore, it is a realization of the invention that if the indication of the dicrotic notch exceeds a set threshold, especially for a pregnant woman in mid- or late pregnancy, it may e.g. be an indication that vascularization of the uterus and the placenta is insufficient and that there is a risk of development of pre-eclampsia or IUGR in the pregnant woman. Thus, the threshold may be set such that the indication of a dicrotic notch exceeding the threshold may be related to development of pre-eclampsia or fetal IUGR.

According to an embodiment, the filtering uses a band-pass filter having a lower cut-off frequency in a range of 100-300 Hz and an upper cut-off frequency in a range of 300-20 000 Hz.

The analysis of the acquired vascular sound signal may comprise filtering the signal using a band-pass filter so as to isolate the frequencies that carry information of the vascular sound of interest. It is therefore desired to isolate frequencies for which the vascular sound is most prominent. This may typically be achieved by a band-pass filter having a bandwidth of 100-1000 Hz, or 200-800 Hz. However, it should be realized that the bandwidth of the band-pass filter may be varied by changing the lower cut-off frequency and/or the upper cut-off frequency, while the desired frequencies are being isolated. It is to be understood that the entire band-pass filtering effect or at least a part of it may be provided by the acoustical and/or mechanical design of the sound and vibration transducer. Thus, it may be preferred to use a specially designed sound and vibration transducer with frequency characteristics serving to suppress sound outside the most important frequency range, which may eliminate or at least supplement the need for a band-pass filter as part of the processing.

According to an embodiment, analyzing the filtered sound signal comprises: forming an envelope curve of the vascular sound signal; and determining a characteristic in the envelope so as to determine an indication of a dicrotic notch in the vascular sound.

The envelope curve provides a representation of the vascular sound signal which allows relevant characteristics to be extracted. Hence, the forming of an envelope curve facilitates making decisions based on the analysis of the filtered sound signal.

There are a number of different characteristics that may be extracted from the envelope curve. According to an embodiment, determining a characteristic comprises deciding whether a critical point is present between a global maximum in a single wave form of the envelope corresponding to a heartbeat and an end of the single wave form. This implies that it is determined whether a dicrotic notch affects the envelope curve such that a portion of the curve is at least flat.

According to another embodiment, determining a characteristic comprises differentiating the envelope of the vascular sound signal to calculate a derivative of the envelope; and determining a maximum of the derivative between a global maximum in a single wave form of the envelope corresponding to a heartbeat and an end of the single wave form as an indication of a dicrotic notch. Hence, the indication of the dicrotic notch may be related to the derivative of the envelope. According to one embodiment, the set threshold corresponds to the maximum of the derivative being zero. This implies that the determination of the derivative of the envelope curve may be used for determining if a critical point is present in the envelope curve.

According to another embodiment, determining a characteristic comprises determining a rise time in a single wave form of the envelope corresponding to a heartbeat as a time from a start of the single wave form to a global maximum in the single wave form; determining a decay time in the single wave form as a time from the global maximum in the single wave form to the end of the single wave form; and comparing the decay time to the rise time to form a relative decay time as an indication of a dicrotic notch. The decay time may be lengthened when the effect of the dicrotic notch is accentuated in the envelope curve. Hence, the comparison of the decay time to the rise time may provide a useful indication of the dicrotic notch. According to one embodiment, the relative decay time may be formed by dividing the decay time with the rise time. Further, the set threshold corresponds to the relative decay time and is set to be in the range of 1.0-5.0.

The analysis of the filtered sound signal may further comprise determining further characteristics in the envelope so as to form further measures of a dicrotic notch. Such further measures may be used for providing further information on the condition of the person. The further measures may optionally be correlated to corresponding thresholds in order to help in identifying a condition of the person that would need to cause an alert to be provided to the person or to a caregiver. Such a further measure may e.g. be the presence of high frequency murmurs in the sound signal, which may be an effect of turbulent bloodflow.

According to one embodiment, the analysis further comprises determining a local maximum and a local minimum between a global maximum in a single wave form of the envelope corresponding to a heartbeat and an end of the single wave form; and determining a dicrotic notch amplitude as the difference of the signal value between the local maximum and the local minimum, said amplitude forming a further measure of the dicrotic notch. The analysis may further comprise determining a heartbeat amplitude as a difference of the signal value between a global minimum and a global maximum in the single wave form, and comparing the dicrotic notch amplitude to the heartbeat amplitude to form a relative amplitude as a further measure of the dicrotic notch. Hence, the amplitude of the envelope curve may be analyzed for providing further information on the effect of the dicrotic notch on the envelope curve.

According to another embodiment, the analysis further comprises determining a local maximum between a global maximum in a single wave form of the envelope corresponding to a heartbeat and an end of the single wave form; and determining a peak delay time as a time between the global maximum and the local maximum, said peak delay time forming a further measure of the dicrotic notch. The analysis may further comprise determining a rise time in the single wave form as a time from a start of the single wave form to the global maximum in the single wave form; and comparing the peak delay time to the rise time to form a relative time of the dicrotic notch as a further measure of the dicrotic notch. Hence, the timing of features in the envelope curve may be analyzed for providing further information on the effect of the dicrotic notch on the envelope curve.

According to another embodiment, the analysis further comprises determining a local maximum and a local minimum between a global maximum in a single wave form of the envelope corresponding to a heartbeat and an end of the single wave form; determining a dicrotic notch area as an area defined between the envelope curve and a straight line at the signal value of the local minimum from the local minimum to a later point on the envelope curve crossing the signal value of the local minimum, said dicrotic notch area forming a further measure of the dicrotic notch. The analysis may further comprise determining a heartbeat area as an area under the envelope curve from the start to the end of the single wave form; and comparing the dicrotic notch area to the heartbeat area to form a relative area of the dicrotic notch as a further measure of the dicrotic notch. Hence, the size of an area in relation to the dicrotic notch may be analyzed for providing further information on the effect of the dicrotic notch on the envelope curve.

According to an embodiment, the analysis of the filtered sound signal may comprise identifying a sequence of wave forms, wherein each single wave form corresponds to a heartbeat and extends from a first local minimum to a second local minimum in the envelope. Then, the indication of the dicrotic notch may be determined based on a plurality of wave forms in order to provide better accuracy to the analysis.

According to one embodiment, determining a characteristic in the envelope comprises determining a characteristic of each single wave form in the sequence of wave forms. Hence, the characteristic for several wave forms may be compared to the set threshold, whereby a percentage of wave forms for which the indication of the dicrotic notch exceeding the threshold may be determined. This allows relating the condition of the person to the frequency with which an indication of the dicrotic notch occurs.

However, there is a realization of the invention that a single wave form may be too noisy and that characteristics determined based on a single wave form may therefore not be as reliable as desired. Therefore, it may be desired to obtain signals which provide stable and precise measurements for making a reliable determination whether an indication of a dicrotic notch in the vascular sound exceeds a set threshold.

According to another embodiment, the method further comprises normalizing each wave form in the sequence of wave forms to a common norm; and computing an average wave form based on the normalized wave forms; wherein determining a characteristic in the envelope comprises determining a characteristic of the average wave form. Hence, the indication of the dicrotic notch may be based on an average over a plurality of wave forms in order to not let analysis be based on a single wave form corresponding to a single heartbeat.

According to another embodiment, the method further comprises selecting wave forms in the sequence of wave forms, wherein the selected wave forms are validated as representing a typical wave form; aligning the selected wave forms, and forming an average wave form of the aligned wave forms.

Thus, the method provides that an average of the wave forms may be formed such that the characteristics of the vascular sound may be accentuated and reliably assessed. In particular, not all wave forms in a sequence of wave forms may be selected. Thus, wave forms that are highly divergent and which may make it difficult to analyze the vascular sound are not allowed to interfere with the analysis.

Further, the selected wave forms are aligned, which may imply that all the selected wave forms are e.g. fitted to a common time scale so that characteristics of the wave forms will be constructively strengthened when the selected wave forms are combined.

Then, an average may be formed from the aligned wave forms so as to smooth small irregularities of the respective selected wave forms and provide an average wave form which may allow for stable and precise analysis.

It should be realized that the average wave form may then be used in a similar manner as described for a single wave form above in order to extract characteristics from the envelope curve.

The method may further comprise comparing the determined characteristic to a historic characteristic previously determined for the person. Hence, the result of the analysis may be compared to historic results for the person so as to enable detection of a deteriorated condition of the person. For instance, an indication of the dicrotic notch exceeding a set threshold may be observed in one of the left and right uterine arteries for a pregnant woman, whereas the indication of the dicrotic notch does not exceed a set threshold for the other uterine artery. In such case, the vascular sound of the other uterine artery may be monitored. If an indication of the dicrotic notch exceeding the set threshold is observed, it may be concluded that the condition of the pregnant woman and/or the fetus has deteriorated.

The method may further comprise using a further sound and vibration transducer to acquire a heartbeat sound signal corresponding to sounds of the heartbeat of the person; cancelling influence of the heartbeat sound on the vascular sound by filtering the vascular sound signal using the heartbeat sound signal. This implies that sounds from the heartbeat of the person may be filtered out in order for the heartbeat not to disturb the measurement of the vascular sound.

The method may further comprise triggering an alert signal in response to the indication of a dicrotic notch in the vascular sound exceeding the set threshold. Hence, when the indication of the dicrotic notch exceeds the set threshold the person may be immediately informed. As an alternative, the alert signal may be transmitted directly to a hospital or clinic.

According to an embodiment, the sound and vibration transducer and the processing unit are arranged in a portable unit which is wearable by the person. This implies that the person may bring the portable unit with him or her at all times, such that the condition of the person may be continuously monitored during daily life.

According to another embodiment, the device may further comprise a communication unit for communicating a signal from the processing unit to a remote unit in dependence of whether the indication of the dicrotic notch exceeds the set threshold. This implies that the processing unit may send a signal to a remote unit when the indication of the dicrotic notch exceeds the threshold. For instance, the signal may be sent to a computer of a hospital or clinic in order to provide an alert that the condition of the person may need attention.

The device may further comprise an indicator, which is connected to the processing unit and which is selectively activated in dependence of whether the indication of the dicrotic notch exceeds the set threshold. This implies that the person may be alerted by means of the indicator when the indication of the dicrotic notch exceeds the set threshold.

According to an embodiment relating to the assessment and/or monitoring of a pregnant woman or a fetus in the pregnant woman, the method may further comprise using a plurality of sound and vibration transducers, which each detect a vascular sound signal, wherein the plurality of sound and vibration transducers are positioned differently in relation to the abdominal or pelvic region of the pregnant woman. It may be difficult to position a single sound and vibration transducer such that a signal of good quality may always be obtained. In particular, movements of the fetus may affect at which position in relation to the abdominal or pelvic region of the pregnant woman an optimal signal may be obtained. Hence, using a plurality of sound and vibration transducers increases the possibility of acquiring a signal that may be properly analyzed.

According to one embodiment, the method further comprises determining a quality of the vascular sound signal from each of the plurality of sound and vibration transducers, and selecting one of the plurality of sound and vibration transducers based on said quality for providing the vascular sound signal to be analyzed. This implies that the sound and vibration transducer that currently gives the best quality signal will be used.

According to another embodiment, the method further comprises forming an average vascular sound signal based on the signal from each of the plurality of sound and vibration transducers. This implies that a stable signal may be obtained regardless whether the quality of a single sound and vibration transducer deteriorates.

It may also be contemplated that a plurality of sound and vibration transducers are used and placed in anatomically different positions. This may allow measuring a pulse wave velocity. For example, the sound and vibration transducers may be positioned in relation to the carotid and the femoral arteries, respectively, or, for a pregnant woman, in relation to the carotid and uterine arteries, respectively.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

The invention will first be described in relation to particular application, wherein vascular sound signals are acquired for analysis in relation to a pregnancy.

Figure 1:
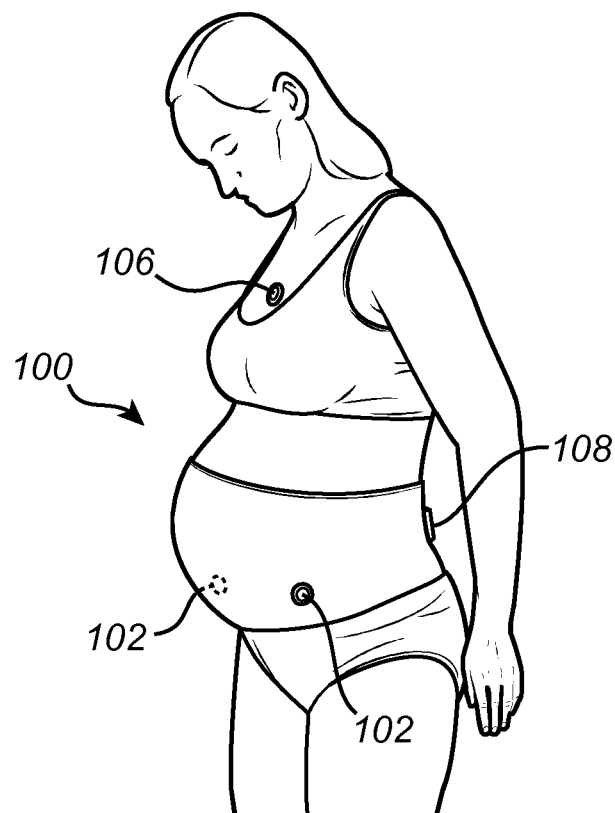
FIG. 1 schematically shows a monitoring device according to an embodiment of the invention as worn by a pregnant woman.

FIG. 1 schematically shows a pregnant woman wearing a monitoring device 100. The monitoring device 100 comprises a sound and vibration transducer 102, which is arranged to be positioned in relation to an abdominal or pelvic region of the pregnant woman. The sound and vibration transducer 102 may be arranged to face the skin of the pregnant woman in order to acquire sound signals from the abdominal or pelvic region of the pregnant woman, such as vascular sound from a uterine artery, an umbilical artery or an iliac artery.

The sound and vibration transducer 102 may be implemented as a microphone and air coupler. The air coupler faces the skin in order to translate a vibration on the surface of the skin to a varying small air pressure inside a chamber of the coupler. The microphone may be arranged in the chamber so as to record the air pressure variations to an electrical signal.

The sound and vibration transducer 102 may be integrated in an adhesive patch that may be attached to the woman's skin for positioning the sound and vibration transducer 102. Alternatively, the sound and vibration transducer 102 may be integrated in a cloth that may be worn by the pregnant woman and properly positions the sound and vibration transducer 102 in relation to the abdominal or pelvic region of the pregnant woman.

However, the sound and vibration transducer may be arranged in a number of different manners for detecting the signal as air pressure variations or as vibrations on the skin surface. For instance, the sound and vibration transducer 102 may be implemented as an accelerometer, which may be attached to the surface of the skin using double adhesives, or a piezoelectric sensor in the form of a piezo bender, which may be attached to the skin.

The monitoring device 100 may thus be worn by the pregnant woman during daily life. The monitoring device 100 may thus continuously monitor a condition of the pregnant woman or the fetus in the pregnant woman. The sound and vibration transducer 102 may thus be arranged to continuously acquire signals or to intermittently acquire signals to periodically check the condition of the pregnant woman or the fetus in the pregnant woman. By means of the monitoring device 100, a deterioration of the condition of the pregnant woman or the fetus in the pregnant woman may be immediately or almost immediately detected. The monitoring device 100 may be arranged to only provide an output signal when a condition meeting a set threshold is detected. In such case, an alert may be given to the pregnant woman and/or a message may be communicated to a hospital or clinic providing information on the condition. Hence, the monitoring device 100 may provide assurance to the pregnant woman, while not requiring human resources of the hospital or clinic for examining the pregnant woman.

The monitoring device 100 may also be utilized at a hospital or clinic, e.g. during childbirth. The monitoring device 100 may thus be positioned for monitoring the condition of the pregnant woman or the fetus. An operator may place the sound and vibration transducer 102 so as to ensure that a strong signal of vascular sound may be obtained. However, thereafter there is no need for an operator handling the monitoring device 100 and, possibly, obstructing a clinician's work. The monitoring device 100 may automate the monitoring of the condition of the pregnant woman or the fetus so as to provide supporting input to a clinician.

The sound and vibration transducer 102 may be positioned so that a signal corresponding to vascular sound may be acquired and converted to an electrical signal, which may later be digitalized and analyzed.

The monitoring device 100 may comprise a plurality of sound and vibration transducers 102, which may be differently positioned in relation to the abdominal or pelvic region of the pregnant woman. Hence, the sound and vibration transducers 102 may acquire signals of vascular sound from different positions, which implies that a quality of the signal may differ between the different sound and vibration transducers 102. The quality of a signal may be dependent on the position of the fetus and, therefore, it may not be known at what position in relation to the abdominal or pelvic region a highest quality signal may be acquired. The signals from the plurality of sound and vibration transducers 102 may be combined for analysis of the vascular sound or the best signal corresponding to the signal from one of the sound and vibration transducers 102 may be used, as described in further detail below. The positioning of the plurality of sound and vibration transducers 102 may be advantageously controlled by a cloth worn by the pregnant woman. Alternatively, the plurality of sound and vibration transducers 102 may be positioned by a caregiver during a visit by the pregnant woman to a hospital or clinic.

The monitoring device 100 may further comprise a heart sensor 106, which may be implemented as a further sound and vibration transducer that is positioned for acquiring a sound from the heartbeat of the pregnant woman. Also, the monitoring device 100 may further comprise an ambience sensor 108 for acquiring sounds from the surroundings. The signal from the heart sensor 106 and/or the signal from the ambience sensor 108 may be used for cancellation of noise in the signal from the sound and vibration transducer 102.

Figure 2:
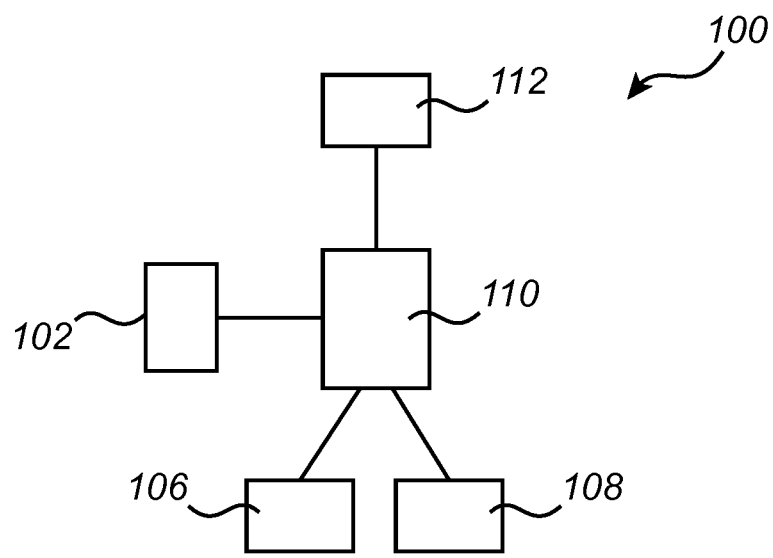
FIG. 2 is a schematic view of a monitoring device according to an embodiment of the invention.

Referring now to FIG. 2, the monitoring device 100 will be further described. The monitoring device 100 further comprises a processing unit 110, which is connected to the sound and vibration transducer 102 for receiving a vascular sound signal.

The processing unit 110 and the sound and vibration transducer 102 may be arranged in a common housing, and the processing unit 110 may thus be arranged to receive a vascular sound signal from the sound and vibration transducer 102 through a wire within such a common housing. However, the processing unit 110 may be arranged in a separate housing, which may be arranged to be worn or carried by the pregnant woman. The processing unit 110 may thus be connected to the sound and vibration transducer 102 with wires for receiving a vascular sound signal. Alternatively, the sound and vibration transducer 102 may comprise a wireless communication unit for wirelessly transferring the vascular sound signal to the processing unit 110.

The processing unit 110 may further be divided into several physical entities such that certain processing may be performed in one entity and other processing may be performed in another entity. For instance, a part of the processing unit 110 may be arranged in a common housing with the sound and vibration transducer 102 for performing first signal processing on the vascular sound signal. Then, the processed vascular sound signal, which may be reduced in size, may be transferred, possibly wirelessly, to the other entity for further processing. Hence, the amount of information that is to be transferred may be reduced.

A part or the entire processing unit 110 may be arranged in a mobile phone or other computing device that the pregnant woman may be carrying.

Hence, the mobile phone may be provided with an application, which may also provide a user interface for viewing results of the monitoring or communicating information to the pregnant woman, if necessary.

The processing unit 110 may further be connected to a memory for storing results and/or logging events that have occurred. Such results may later be accessed by a caregiver, e.g. when the pregnant woman visits a hospital or clinic, so that the results may be analyzed by the caregiver.

The monitoring unit 100 may further comprise an indicator in the form of an output device 112 for providing output to a user. In this regard, the output device 112 may comprise a display for displaying messages to the pregnant woman, in the form of text messages or by turning on or off symbols on the display. Alternatively, or additionally, the output device 112 may comprise one or more lamps, which may communicate information to the pregnant woman by being turned on or off. For instance, a green lamp may communicate that all is OK, while a red lamp may communicate that contact with a hospital should be taken. Alternatively, or additionally, the output device 112 may comprise a horn or loudspeaker for providing an audio signal and/or a vibrator for providing a tactile signal to the pregnant woman.

Figure 3:
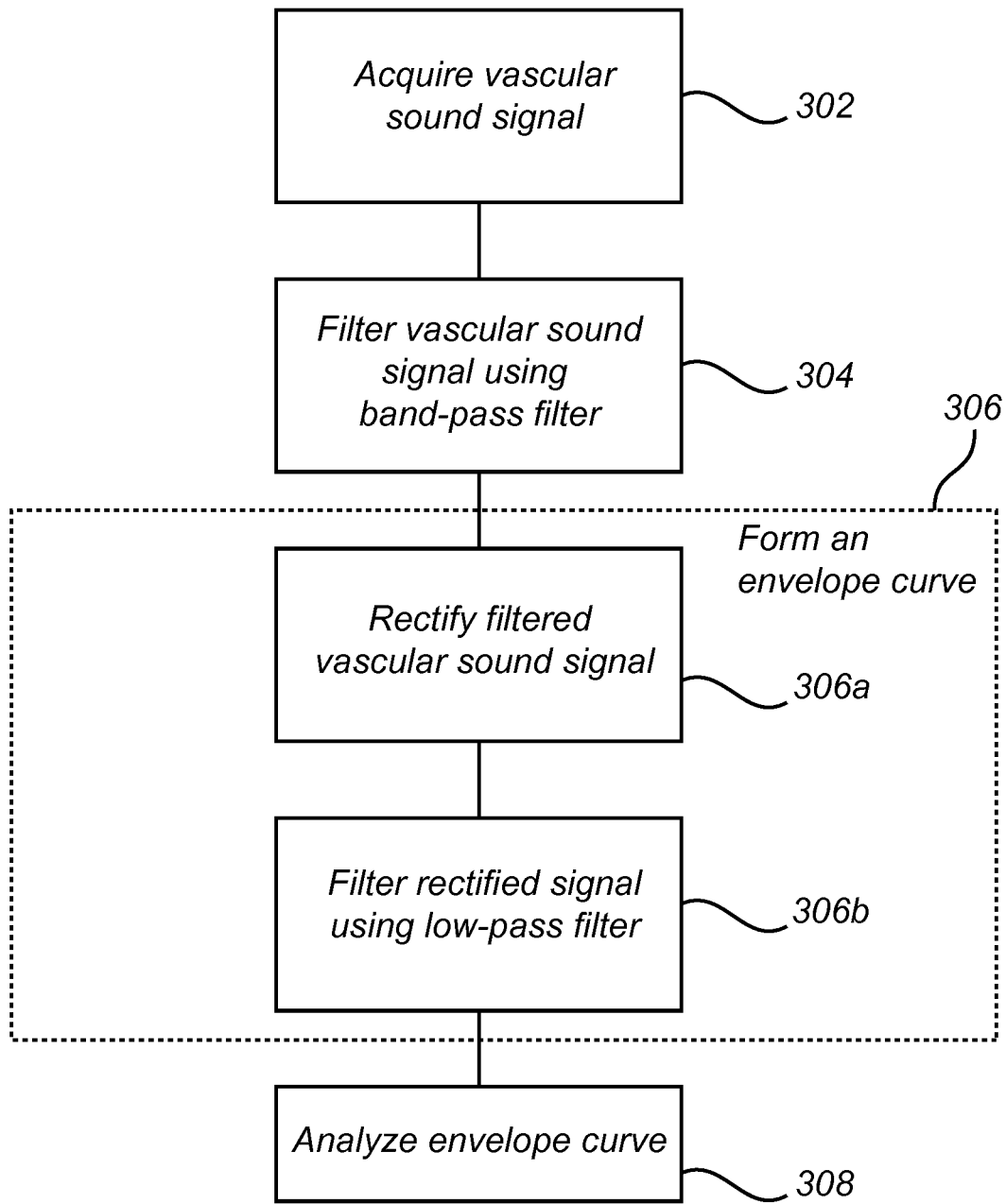
FIG. 3 is a flow chart of a method of processing a vascular sound signal according to an embodiment of the invention.

Referring now to FIG. 3, processing of the vascular sound signal will be further described. A vascular sound signal is acquired, step 302, using a sound and vibration transducer 102. If a plurality of sound and vibration transducers 102 is used, a quality measure of the signals from the different sound and vibration transducers 102 may be examined in order to select the signal of best quality for further processing. For instance, such quality measure may be a signal-to-noise ratio. Then, the selected signal is provided for further processing. Alternatively, the signals from a plurality of sound and vibration transducers 102 may be averaged in order to create a combined signal, which is provided for further processing.

The vascular sound signal is then filtered, step 304, using a band-pass filter. The band-pass filter may isolate frequencies that enable analysis of the vascular sound. In such regard, the band-pass filter may have a lower cut-off frequency to filter out disturbing low frequency sounds, which may include sounds originating from fetal heartbeat. The lower cut-off frequency may be arranged in a range of 100-300 Hz, preferably in a range of 100-200 Hz. In one embodiment, the lower cut-off frequency may be set to 180 Hz. The upper cut-off frequency may be arranged in a range of 300-20 000 Hz, preferably in a range of 600-1 500 Hz. In one embodiment, the upper cut-off frequency may be set to 650 Hz.

The entire band-pass filtering effect or at least a part of it may be provided by the acoustical and/or mechanical design of the sound and vibration transducer 102, such that at least part of the filtering may be accomplished in the acquiring of the vascular sound signal by means of the design of the sound and vibration transducer 102. Thus, it may be preferred to use a specially designed sound and vibration transducer 102 with frequency characteristics serving to suppress sound outside the most important frequency range. In particular, the sound and vibration transducer 102 may be arranged to only detect frequencies below a specifically designed cut-off frequency. For instance, the sound and vibration transducer 102 may be arranged to detect frequencies below 1 500 Hz, which may eliminate a need for filtering out high frequencies, since such are not part of the signal acquired by the sound and vibration transducer 102. Hence, the signal processing may use a high-pass filter with a cut-off frequency in the range of 100-300 Hz, utilizing that undesired high frequencies are never acquired into the signal by the sound and vibration transducer 102.

The band-pass filtering may be accomplished by means of signal processing by the processing unit 110. The vascular sound signal may be passed through an analog-to-digital conversion before the band-pass filtering, such that the band-pass filter is applied to a digital signal. The analog-to-digital conversion may be provided in the sound and vibration transducer 102 or in the processing unit 110.

The vascular sound signal may also be filtered by making use of the signals acquired by the heart sensor 106 and the ambience sensor 108. The signals from these sensors may be used for noise cancellation in the vascular sound signal. Noise cancellation filtering may be achieved by applying an adaptive filter to the vascular sound signal using the signal from the heart sensor and/or ambience sensor as input. For instance, Wiener-filtering of the vascular sound signal may be used. The noise cancellation filtering may be performed before or after the vascular sound signal is filtered using the band-pass filter.

An envelope curve of the band-pass filtered vascular sound signal is formed, step 306. The envelope curve may be formed by rectifying the filtered vascular sound signal, step 306*a*, so as to provide absolute values of the signal. The rectified signal may be further filtered, step 306*b*, using a low-pass filter in order to provide smoothing of the signal curve. The low-pass filter may have a cut-off frequency within the range 1-20 Hz, such as within the range 2-15 Hz, such as within the range 3-10 Hz, such as within the range 4-8 Hz. The envelope curve may be formed in a number of alternative ways. For instance, the envelope curve may be formed by performing a Hilbert transform on the filtered vascular signal and smoothing the curve.

Alternatively, homomorphic filtering may be performed. As a further alternative, a normalized average Shannon energy method may be used to obtain the envelope curve. It should be realized that any other method of forming the envelope curve known to the skilled person may be used.

The envelope curve may then be analyzed, step 308, in order to determine a condition of the pregnant woman or the fetus. In this regard, a characteristic of the envelope curve providing an indication of a dicrotic notch may be determined as will now be further described with reference to FIG. 4.

Figure 4:
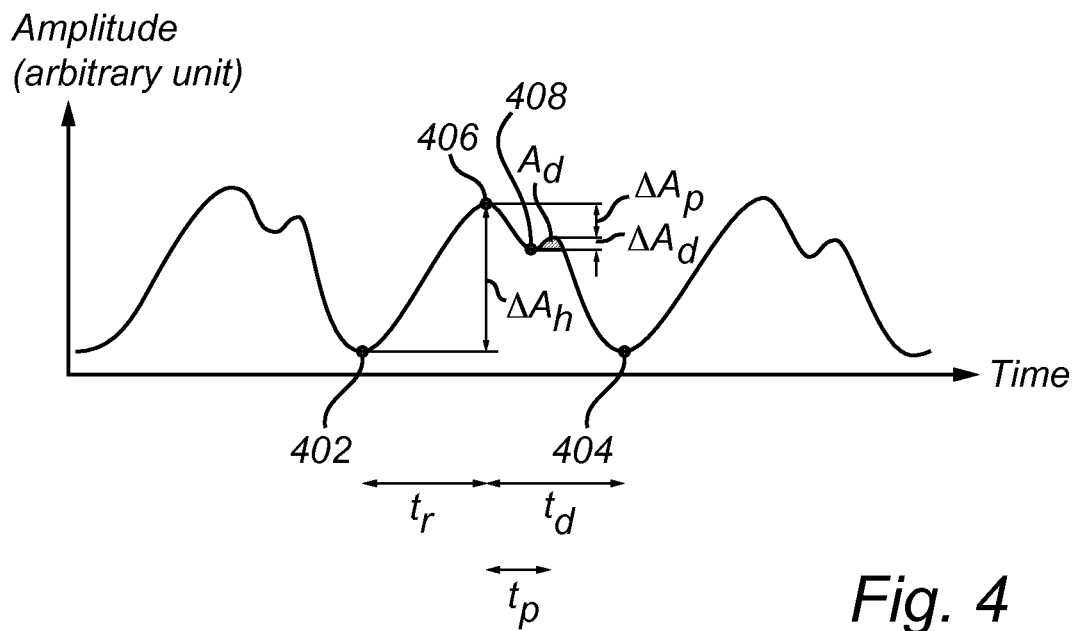
FIG. 4 is a schematic view of an envelope curve that is formed from the acquired vascular sound signal.

FIG. 4 schematically shows an envelope curve of an acquired signal of vascular sound from a pregnant woman. The envelope curve provides an amplitude of the vascular sound signal over time. The envelope curve provides a sequence of wave forms, each corresponding to a heartbeat. A single wave form starts with a minimum in the envelope curve and ends with a corresponding minimum as indicated by points 402 and 404, respectively.

The single wave form comprises a global maximum, i.e. a maximum within the single wave form, as indicated by point 406. This maximum corresponds to a maximum vascular blood flow during a cardiac cycle. After the maximum vascular blood flow is reached, a dip in aortic pressure occurs in the cardiac cycle and coincides with the closure of the aortic valve. This causes a temporal dip in the blood flow as well as indicated by point 408, and is called a dicrotic notch.

The single wave form may be analyzed in order to determine a characteristic which provides an indication of the dicrotic notch. The characteristic may be compared to a set threshold and a value of the characteristic exceeding the set threshold may be used for providing a diagnosis.

Although reference is made below to a single wave form, it should be realized that an average wave form which may be formed from a plurality of single wave forms may be analyzed instead and that the analysis described to be performed on a single wave form may instead be performed on an average wave form. The forming of an average wave form will be further described below.

When acquiring vascular sound originating from a uterine artery, an umbilical artery or an iliac artery in a pregnant woman, the effect of the dicrotic notch on the blood flow may be detected. After gestational week 24, the effect of the dicrotic notch on the blood flow in the uterine, umbilical and iliac arteries is normally insignificant, since the uterine arteries have gone through structural enlargement during the pregnancy. Therefore, an indication of the dicrotic notch exceeding a set threshold may at least after this stage of pregnancy be an indication of an insufficient vascularization of the uterus or the placenta, which may be correlated to development of pre-eclampsia or IUGR. Hence, the monitoring device 100 may advantageously be used for assessment of the condition of a pregnant woman and/or the fetus during mid- or late pregnancy.

The analysis of the single wave form may include differentiating the single wave form in order to analyze the first derivative of the envelope curve. A zero crossing of the first derivative between the global maximum and the end of the single wave form may be determined as a characteristic being an indication of the dicrotic notch. In other words, if the first derivative between the global maximum and the end of the single wave form exceeds zero, the indication of the dicrotic notch exceeds the threshold, which may indicate a condition of the pregnant woman or the fetus requiring further actions.

The analysis of the single wave form may additionally or alternatively comprise analyzing the second derivative of the envelope curve. The maximum and minimum of the first derivative may be determined by the second derivative and used for further analysis as characteristics being an indication of the dicrotic notch. These characteristics may then be compared to set thresholds for determining whether the indication exceeds the threshold, which may indicate a condition of the pregnant woman or the fetus requiring further actions.

The analysis of the single wave form may additionally or alternatively comprise determining a rise time tr from the start point 402 to the global maximum 406 and a decay time td from the global maximum 406 to the end point 404. The decay time td may be compared to the rise time tr to form a relative decay time, e.g. by dividing the decay time td with the rise time tr. This relative decay time may be used as an indication of the dicrotic notch and may be compared to a set threshold for determining whether the indication exceeds the threshold. The threshold may be set to be in a range of 1.0-5.0, e.g. 2.0, such that if the determined relative decay time is larger than the threshold, the indication of the dicrotic notch exceeds the set threshold and further action may be required.

The analysis of the single wave form may further comprise determining further measures relating to the dicrotic notch. Such further measures may be used for determining that a condition of the pregnant woman or the fetus requires further action or may be used to provide further information about the condition when another indication of the dicrotic notch has been determined to exceed a set threshold, as described above. The further measures may quantify the dicrotic notch and may provide measures on the severity of the effect as presented in the vascular sound signal.

A local minimum and a local maximum may be determined in the wave form between the global maximum and the end of the wave form. The local minimum and maximum may be determined by means of differentiating the envelope curve. The local minimum and local maximum may be considered to relate to the dicrotic notch. The local minimum does in fact correspond to the critical point, as discussed above.

Then, the difference in amplitude Md between the local minimum and the local maximum may be determined forming a measure of the dicrotic notch. Also, a second difference in amplitude in the wave form may be determined such that the difference in amplitude of the dicrotic notch Md may be related to the second difference. The second difference in amplitude may be a heartbeat amplitude being a difference in amplitude Mh between the start of the wave form and the global maximum of the wave form. Alternatively, the second difference in amplitude may be a difference in amplitude Mp between the global maximum and the local maximum relating to the dicrotic notch. A relative amplitude of the dicrotic notch may be determined by dividing the amplitude of the dicrotic notch Md with the second difference in amplitude. The relative amplitude may then form a measure of the dicrotic notch.

Further, a peak delay time tp may be determined as a time between the global maximum and the local maximum relating to the dicrotic notch. The peak delay time tp may form a measure of the dicrotic notch. Further, the peak delay time tp may be compared to a second time measured in the wave form, such as the rise time tr. For instance, a relative time of the dicrotic notch may be determined by dividing the peak delay time tp with the second time measured. The relative time of the dicrotic notch may then form a measure of the dicrotic notch.

Further, an area Ad in the wave form relating to the dicrotic notch may be determined. The dicrotic notch area Ad may be defined as an area between the envelope curve and a straight line at the signal value of the local minimum, from the local minimum to a later point on the envelope curve, where the envelope curve crosses the straight line. The dicrotic notch area Ad may form a further measure of the dicrotic notch. Also, the dicrotic notch area Ad may be compared to a second area under the envelope curve. For instance, a second area may be determined as the entire area under the envelope curve from the start to the end of the wave form. A relative area of the dicrotic notch may be determined by dividing the dicrotic notch area Ad with the second area. The relative area may then form a measure of the dicrotic notch.

A plurality of sequential wave forms may be determined in the envelope curve. The plural wave forms may then be normalized according to some characteristic, such as a global maximum value, and the normalized wave forms may then be used for forming an average wave form. This average wave form may be analyzed as described above for a single wave form, such that the analysis does not overemphasize the sound acquired corresponding to a single heartbeat.

An embodiment for forming the average wave form will now be further described.

Firstly, an envelope curve is formed for a plurality of sequential wave forms. Wave forms representing single heart beats are extracted from the envelope curve. The wave forms are then analyzed according to a criterion for determining whether an analyzed wave form should be allowed to contribute in forming an average wave form.

The analysis to determine whether a wave form should contribute to the average wave form may be based on a template. The wave form is compared to the template and is rejected when a correlation of the wave form to the template is below a set threshold. Thus, wave forms that differ too much from the template will not be included in the forming of the average wave form, such that the average wave form that will be formed will emphasize the common characteristics of the wave forms and allow forming a signal with a good signal-to-noise ratio.

Wave forms that have a sufficiently high correlation to the template are validated as representing a typical wave form within the acquired vascular sound signal. These wave forms are selected to be included in the forming of the average wave form.

The template may be based on a single heart beat within the envelope curve. The single heart beat may be validated against a standard wave form to ensure that the wave form of the single heart beat in the envelope curve may be properly used as a template. This implies that the template is based on the acquired vascular sound signal and that wave forms that are similar within the envelope curve will be used for forming the average wave form. The template may also be updated with information from further wave forms within the envelope curve that are selected to be included in the forming of the average wave form.

The template may be formed by detecting a peak within the envelope curve and extracting a segment around the detected peak so as to obtain a wave form representing a single heartbeat.

According to an alternative, a template may be stored in association with the person from whom the vascular sound signal was acquired. This implies that the template may be re-used when acquiring vascular sound signals at later occasions allowing the analysis of the vascular sound to be compared over time.

As a further alternative, one or more templates may be generally used such as to allow comparison between different persons. However, such a general template may make it more difficult to select wave forms to be included in the forming of the average wave form, since a large ratio of wave forms in the plurality of sequential wave forms may not be sufficiently similar to the template in order to be selected.

The selected wave forms may then be aligned so that a combination of the selected wave forms should emphasize features that are common to the selected wave forms. The alignment may be performed so as to ensure that the selected wave forms are represented in a common time scale, such that the features of the wave forms are arranged at similar points in time.

Alignment of the selected wave forms may be achieved by representing the selected wave forms on a common time scale, which may be chosen as the duration of one selected wave form, e.g. the wave form used as a template.

Alignment of the selected wave forms may additionally or alternatively be achieved by using one or more features of the wave forms as alignment markers and placing the one or more alignment markers at overlapping times in the wave forms. For instance, the peaks of the wave forms may be used as alignment markers and/or a slope leading to the peak may be used as alignment markers.

Alignment of the selected wave forms may additionally or alternatively include determining a maximum correlation of the selected wave form with the template and aligning the selected wave forms on basis of the maximum correlation.

When the selected wave forms have been aligned, the wave forms are represented in an overlapping manner such that noise in the individual wave forms may be reduced by forming an average wave form.

The average wave form may be formed by computing the average of all selected and aligned wave forms at each point in time. Alternatively, the average wave form may be formed by determining a median value of the selected and aligned wave forms at each point in time.

The average wave form may allow stable and precise measurements for making a reliable assessment based on the acquired vascular sound signal.

As an alternative, each of a plurality of sequential wave forms is analyzed as described above for a single wave form. A characteristic in the envelope may be determined for each wave form in order to determine an indication of the dicrotic notch. Further, a percentage or number of wave forms for which the indication of the dicrotic notch exceeds the set threshold may be determined. Based on the determined percentage or number of wave forms a decision may be taken whether further action may be required. Hence, the analysis need not indicate that a further action is required if the indication of the dicrotic notch exceeds the set threshold in a single wave form. However, if the indication of the dicrotic notch exceeds the set threshold in a large percentage of wave forms, such as in 50% of the analyzed wave forms, the analysis may indicate that a further action is required.

The determined characteristics of the filtered sound signal, as described above, may be combined with any other characteristics that may be determined from the filtered sound signal or may be determined by other means in order to form a decision on the condition of the pregnant woman or the fetus. For instance, a pulsatility index or resistivity index may be determined. Also, presence of high frequency murmurs due to vascular turbulence may be used for forming a decision on the condition of the pregnant woman or the fetus.

Further, an analysis of the filtered vascular sound signal may be performed in a frequency domain. For instance, a Fourier analysis may be performed e.g. by means of computing a Fast Fourier Transform (FFT) of the vascular sound signal. The analysis of the vascular sound signal in the frequency domain may be used for determining characteristics that may be used individually or in combination with other determined characteristics, as described above, in order to form a decision on the condition of the pregnant woman or the fetus.

The determination of characteristics or measures of the envelope curve as described above may be performed by computation steps in the processing unit 110 on a digitalized representation of the envelope curve.

These computation steps may be implemented in software of the processing unit 110, or as hardware in the form of e.g. an Application Specific Integrated Circuit (ASIC) or Field-Programmable Gate Array (FPGA) or any combination of hardware or software.

Figure 5:
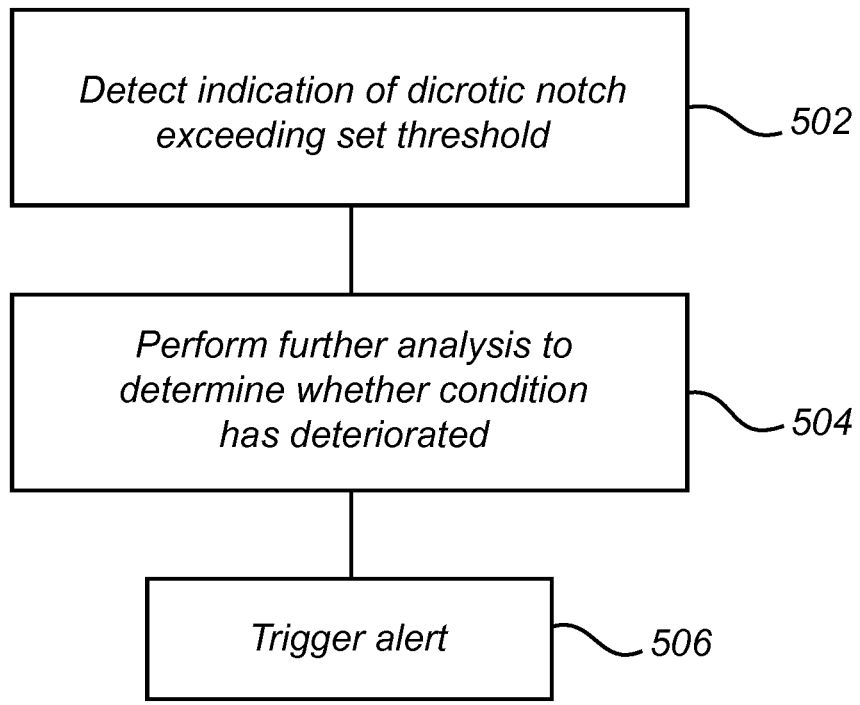
FIG. 5 is a flow chart of a method of acting on a detection of an indication of a dicrotic notch exceeding a set threshold.

Referring now to FIG. 5, the use of a result of the analysis of the vascular sound signal will be further described. The result of an analysis may always be stored or logged in a memory.

When the analysis detects an indication of a dicrotic notch exceeding a set threshold, step 502, this detection may be used as a trigger to determine whether further action is required. A further analysis may optionally be performed, step 504, to determine whether a condition of the pregnant woman or the fetus has deteriorated or is so severe that the pregnant woman should contact a hospital or clinic. The further analysis may comprise comparing the determined indication of the dicrotic notch to historical results of the indication of the dicrotic notch for the pregnant woman, such as a historical result of a dicrotic notch area Ad. Such historical results may be stored locally in the processing unit 110 or in a server that the processing unit 110 may contact. If the determined indication of the dicrotic notch corresponds to historical results of the indication, a decision may be taken that no further action is required.

A historical result may also be that the indication of the dicrotic notch is detected to exceed the set threshold for the vascular sound from one of the left or right uterine arteries of the pregnant woman. For instance, the indication of the dicrotic notch may exceed the set threshold for the left uterine artery, while the indication of the dicrotic notch may not exceed the set threshold for the right uterine artery. In such case, a later detection that the indication of the dicrotic notch exceeds the set threshold for the right uterine artery may be used to conclude that the condition of the pregnant woman and/or the fetus has deteriorated and that further action may be required.

If further action is required, the processing unit 110 may trigger the output device 112 to alert the pregnant woman, step 506, that a condition is detected that may need attention. The output device 112 may thus present a text message or turn on a symbol on a display. Alternatively or additionally, a lamp may be turned on or an audible or tactile signal may be output. The signal may indicate to the pregnant woman that a hospital or clinic should be contacted for further examination of the condition.

The threshold may be set in relation to normal values for the indication of the dicrotic notch in different gestational ages by creation of a database of indications of the dicrotic notch for normal population. Hence, the monitoring of the condition of the pregnant woman and/or the fetus may be related to the gestational age. Since an indication of the dicrotic notch may typically differ between early, mid- and late pregnancy, setting the threshold in relation to the gestational age may facilitate detection of a condition that may require further action.

The use of a sound and vibration transducer 102 may be utilized for assessment and/or monitoring of the cardiovascular health of a person. The sound and vibration transducer 102 may thus be positioned in relation to a region of interest of the person, such as the cervical, thoracic, abdominal, pelvic or lower limb region of the person. The sound and vibration transducer 102 may acquire a vascular sound signal from this region of interest in order to enable assessment and/or monitoring of the cardiovascular health of the person. The acquired signal may then be analyzed in a manner similar to the above description in order to determine whether an indication of a dicrotic notch in the vascular sound exceeds a set threshold. Such an indication may be correlated to a condition of the person requiring attention and an alert may be given.

For instance, screening or monitoring of various hemodynamic scenarios may be achieved, such as hypertension, hypotension, left ventricular dysfunctions, aortic stiffness, physical fitness (in relation to improvement of endothelial functions), and effect of drugs (e.g. vasodilators/constrictors).

The person skilled in the art realizes that the present invention by no means is limited to the preferred embodiments described above. On the contrary, many modifications and variations are possible within the scope of the appended claims.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for assessment and/or monitoring a person's cardiovascular state, the method comprising:
   using a sound and vibration transducer to acquire a vascular sound signal in order to detect a vascular sound from a cervical, thoracic, abdominal, pelvic, or lower limb region of the person;
   filtering the vascular sound signal to isolate the vascular sound, said filtering using a filter which attenuates frequencies below a lower cut-off frequency in a range of 100-300 Hz; and
   analyzing the filtered sound signal in order to determine whether an indication of a dicrotic notch in the vascular sound exceeds a set threshold,
   wherein analyzing the filtered sound signal comprises:
   forming an envelope curve of the vascular sound signal; and
   determining a characteristic in the envelope so as to determine an indication of a dicrotic notch in the vascular sound;
   wherein analyzing the filtered sound signal further comprises:
       identifying a sequence of wave forms, wherein each single wave form corresponds to a heartbeat and extends from a first local minimum to a second local minimum in the envelope; and
       (i) selecting wave forms in the sequence of wave forms, wherein the selected wave forms are validated as representing a typical wave form; aligning the selected wave forms, and forming an average wave form of the aligned wave forms; or (ii) normalizing each wave form in the sequence of wave forms to a common norm; and computing an average wave form based on the normalized wave forms.

2. The method according to claim 1, wherein the sound and vibration transducer is used to detect a vascular sound from an abdominal or pelvic region of a pregnant woman for assessing and/or monitoring the pregnant woman or a fetus in the pregnant woman.

3. The method according to claim 2, further comprising using a plurality of sound and vibration transducers, which each detect a vascular sound signal, wherein the plurality of sound and vibration transducers are positioned differently in relation to the abdominal or pelvic region of the pregnant woman.

4. The method according to claim 3, further comprising determining a quality of the vascular sound signal from each of the plurality of sound and vibration transducers, and selecting one of the plurality of sound and vibration transducers based on said quality for providing the vascular sound signal to be analyzed.

5. The method according to claim 3, further comprising forming an average vascular sound signal based on the signal from each of the plurality of sound and vibration transducers.

6. The method according to claim 1, wherein the filtering uses a band-pass filter having a lower cut-off frequency in a range of 100-300 Hz and an upper cut-off frequency in a range of 300-20 000 Hz.

7. The method according to claim 1, wherein determining a characteristic comprises deciding whether a critical point is present between a global maximum in the average wave form and an end of the average wave form.

8. The method according to claim 1, wherein determining a characteristic comprises differentiating the envelope of the vascular sound signal to calculate a derivative of the average wave form; and determining a maximum of the derivative between a global maximum in the average wave form and an end of the average wave form as an indication of a dicrotic notch.

9. The method according to claim 8, wherein the set threshold corresponds to the maximum of the derivative being zero.

10. The method according to claim 1, wherein determining a characteristic comprises determining a rise time in the average wave form as a time from a start of the average wave form to a global maximum in the average wave form; determining a decay time in the average wave form as a time from the global maximum in the average wave form to the end of the average wave form; and comparing the decay time to the rise time to form a relative decay time as an indication of a dicrotic notch.

11. The method according to claim 1, wherein analyzing the filtered sound signal further comprises determining further characteristics in the envelope so as to form further measures of a dicrotic notch.

12. The method according to claim 11, further comprising determining a local maximum and a local minimum between a global maximum in the average wave form and an end of the average wave form; and determining a dicrotic notch amplitude as the difference of the signal value between the local maximum and the local minimum, said amplitude forming a further measure of the dicrotic notch.

13. The method according to claim 11, further comprising determining a heartbeat amplitude as a difference of the signal value between a global minimum and a global maximum in the single wave form, and comparing the dicrotic notch amplitude to the heartbeat amplitude to form a relative amplitude as a further measure of the dicrotic notch.

14. The method according to claim 11, further comprising determining a local maximum between a global maximum in the average wave form and an end of the average wave form; and determining a peak delay time as a time between the global maximum and the local maximum, said peak delay time forming a further measure of the dicrotic notch.

15. The method according to claim 14, further comprising determining a rise time in the average wave form as a time from a start of the average wave form to the global maximum in the average wave form; and comparing the peak delay time to the rise time to form a relative time of the dicrotic notch as a further measure of the dicrotic notch.

16. The method according to claim 11, further comprising determining a local maximum and a local minimum between a global maximum in the average wave form and an end of the average wave form; determining a dicrotic notch area as an area defined between the envelope curve and a straight line at the signal value of the local minimum from the local minimum to a later point on the envelope curve crossing the signal value of the local minimum, said dicrotic notch area forming a further measure of the dicrotic notch.

17. The method according to claim 16, further comprising determining a heartbeat area as an area under the envelope curve from the start to the end of the average wave form; and comparing the dicrotic notch area to the heartbeat area to form a relative area of the dicrotic notch as a further measure of the dicrotic notch.

18. The method according to claim 1, further comprising comparing the determined characteristic to a historic characteristic previously determined for the person.

19. The method according to claim 1, further comprising using a further sound and vibration transducer to acquire a heartbeat sound signal corresponding to sounds of the heartbeat of the person; cancelling influence of the heartbeat sound on the vascular sound by filtering the vascular sound signal using the heartbeat sound signal.

20. The method according to claim 1, further comprising triggering an alert signal in response to the indication of a dicrotic notch in the vascular sound exceeding the set threshold.

21. A device for assessment and/or monitoring of a person's cardiovascular state, the device comprising:
a sound and vibration transducer, which is arranged to be positioned in relation to a cervical, thoracic, abdominal, pelvic, or lower limb region of the person so as to acquire a vascular sound signal in order to detect a vascular sound from the region of the person; and
a processing unit, which is arranged to receive the vascular sound signal from the sound and vibration transducer and which is further configured to process the vascular sound signal by
filtering the vascular sound signal to isolate the vascular sound, said filtering using a filter which attenuates frequencies below a lower cut-off frequency in a range of 100-300 Hz; and
analyzing the filtered sound signal in order to determine whether an indication of a dicrotic notch in the vascular sound exceeds a set threshold,
wherein analyzing the filtered sound signal comprises:
forming an envelope curve of the vascular sound signal; and
determining a characteristic in the envelope so as to determine an indication of a dicrotic notch in the vascular sound;
wherein analyzing the filtered sound signal further comprises:
identifying a sequence of wave forms, wherein each single wave form corresponds to a heartbeat and extends from a first local minimum to a second local minimum in the envelope; and
(i) selecting wave forms in the sequence of wave forms, wherein the selected wave forms are validated as representing a typical wave form; aligning the selected wave forms, and forming an average wave form of the aligned wave forms; or (ii) normalizing each wave form in the sequence of wave forms to a common norm; and computing an average wave form based on the normalized wave forms.

22. The device according to claim 21, wherein the sound and vibration transducer and the processing unit are arranged in a portable unit which is wearable by the person.

23. The device according to claim 21, further comprising a communication unit for communicating a signal from the processing unit to a remote unit in dependence of whether the indication of the dicrotic notch exceeds the set threshold.

24. The device according to claim 21, further comprising an indicator, which is connected to the processing unit and which is selectively activated in dependence of whether the indication of the dicrotic notch exceeds the set threshold.

* * * * *